United States Patent [19]

Storar

[11] Patent Number: 5,505,078
[45] Date of Patent: Apr. 9, 1996

[54] METHOD AND APPARATUS FOR MEASURING FRICTION TORQUE

[76] Inventor: Robert C. Storar, c/o Automation Technology, Inc. 1900 Troy St., Dayton, Ohio 45404

[21] Appl. No.: 397,979

[22] Filed: Mar. 30, 1995

Related U.S. Application Data

[62] Division of Ser. No. 303,370, Sep. 9, 1994.

[51] Int. Cl.$^6$ .................................................. G01M 15/00
[52] U.S. Cl. .................................................. 73/116
[58] Field of Search ......................... 73/9, 10, 116, 73/862.09; 324/772; 318/490

[56] References Cited

U.S. PATENT DOCUMENTS

| 3,505,863 | 4/1970 | Lucia . | |
|---|---|---|---|
| 3,942,365 | 3/1976 | Hanson et al. | 73/116 |
| 4,204,425 | 5/1980 | Mallick, Jr. . | |
| 4,741,182 | 5/1988 | Didies et al. | 68/12.15 |
| 5,327,790 | 7/1994 | Levin et al. | 73/862.325 |

*Primary Examiner*—Robert Raevis
*Attorney, Agent, or Firm*—Biebel & French

[57] ABSTRACT

Friction torque of a motor undergoing testing is measured by supporting an electrical motor on a test fixture and connecting a torque measuring device to its output shaft. The motor shaft is rotated in the reverse direction and while the motor shaft is freely rotating, power is applied to the motor and two torque measurements are taken to determine friction torque. The first is while the motor is still rotating in the reverse direction, and the second is taken from zero rpm to approximately 50 rpm. In both cases, the torque is measured while the motor shaft is near zero rpm, thus representing locked rotor torque. Half the difference between these two torque measurements will yield the value for friction torque. Motor torque is continued to be measured while the motor is accelerated to its maximum speed, and the value of this measured torque can then be adjusted by the value of the friction torque to provide a measurement of the actual torque of the motor being tested.

1 Claim, 5 Drawing Sheets

METHOD AND APPARATUS FOR MEASURING FRICTION TORQUE

This is a divisional application based upon application Ser. No. 08/303,370, filed Sep. 9, 1994.

BACKGROUND OF THE INVENTION

This invention relates to a method and apparatus for measuring friction torque associated with a motor under test.

Friction torque can result from friction generated in a test fixture by the bearings which support various components of that fixture. For example, when testing electric motors, the motor will be brought into position and coupled to an inertial flywheel which has coupled to it an incremental encoder, as described in U.S. Pat. No. 5,218,860. Friction can also result from misalignment of the motor shaft with respect to the test fixture shaft, thus causing side loading. Another source 15 of friction torque is the result of tight motor bearings; in many cases, the motor bearings will free up after the motor runs for some period of time, however, to obtain an accurate measure of the torque output of a motor, it would be desirable to compensate the measured torque for this initial bearing tightness.

Measuring friction torque would thus allow an accurate determination off the actual torque that can be generated by an electric motor, thus providing a more accurate indication of the quality of the motor itself.

SUMMARY OF THE INVENTION

In the present invention, the actual torque of a motor is determined by first measuring the friction torque of the motor; next, measuring the torque of the motor under test; and finally, adding the friction torque to the measured torque to obtain actual torque.

This accomplished in the present invention by first rotating the motor in a direction reverse to that of its normal rotation, and then by applying power to the motor while it is rotating, thus causing the motor to slow to a stop, reverse direction, and then accelerate in the forward or normal direction to its final operating speed. While the motor is in reverse rotation, both the locked rotor torque TM and the friction torque TF combine to slow the motor shaft to zero. This may be expressed as TM+TF. As the motor accelerates in its normal or forward direction, the measured torque will be the difference between locked rotor torque TM and the friction torque TF; expressed as TM−TF. Friction torque can thus be determined by subtracting these two measured torque values, (TM+TF)−(TM−TF), and dividing by two.

In the present invention, torque is measured by an encoder attached to the output shaft of the motor. The specific mechanism for measuring torque in the preferred embodiment of the invention is described in detail in U. S. Pat. No. 5,218,860 issued Jun. 15, 1993. In that device, torque is a function of the amount of shaft rotation during known time intervals. Thus, torque can be plotted against motor speed, which may also be determined from the encoder output signal.

It is an object of this invention to measure the value of friction torque by imparting a reverse direction rotation to a motor shaft, applying power to the motor, measuring the average torque as the motor slows to zero, measuring the average torque as the motor thereafter accelerates from zero rpm to a predetermined low speed (thus to simulate locked rotor torque), and taking one-half of the difference between these two torque values.

It is another object of this invention to provide a method for determining the actual torque of an electrical motor comprising the steps of determining the friction torque of a motor under test, measuring the torque of the motor under test, and adding the friction torque to the measured torque to obtain the actual torque.

Other objects and advantages of the invention will be apparent from the following description, the accompanying drawings and the appended claims.

DESCRIPTION OF THE PREFERRED EMBODIMENT

Figure 1:
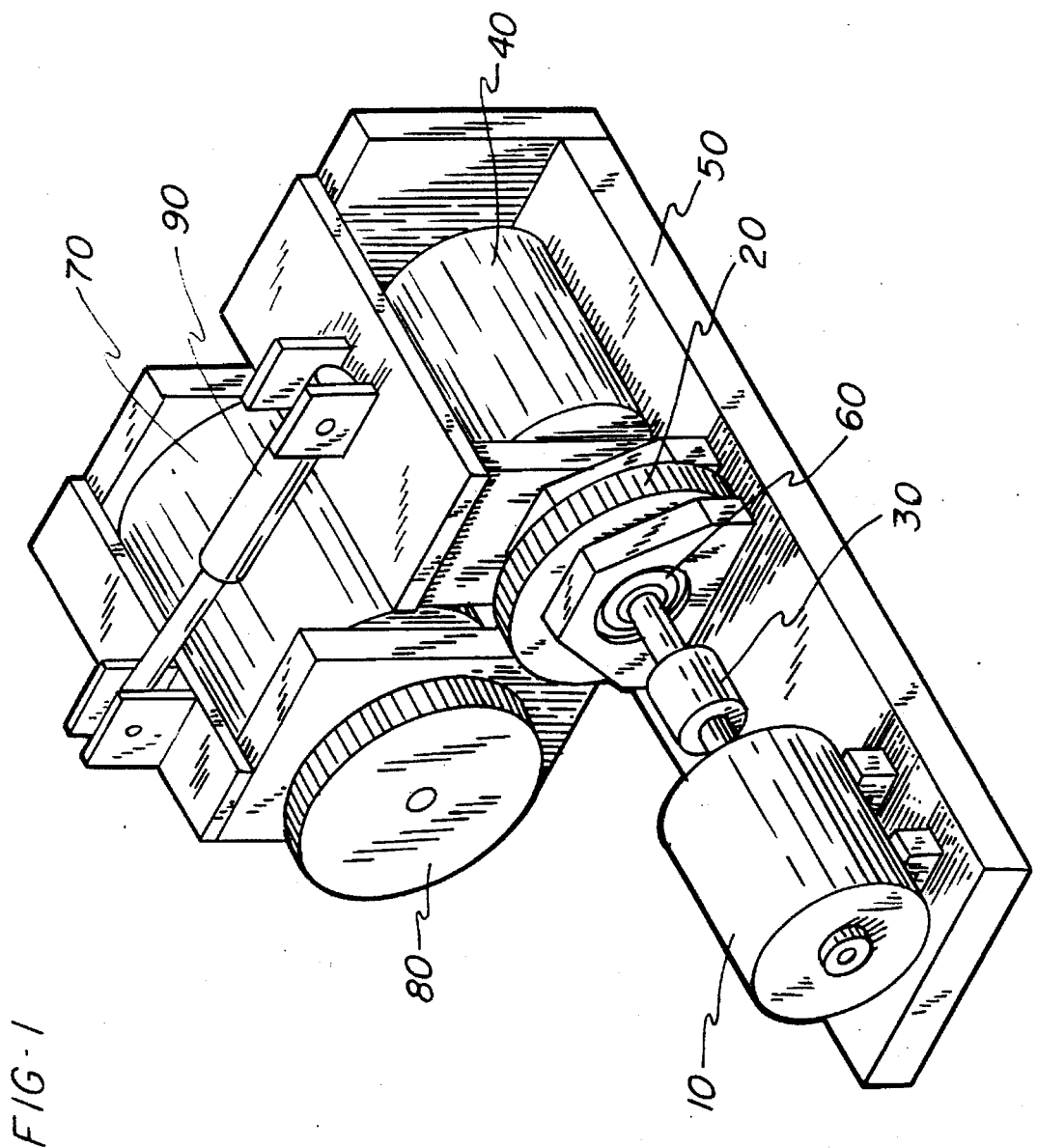
FIG. 1 is a perspective schematic view of a preferred embodiment of the invention showing a motor under test attached to a flywheel and digital encoder with a back drive motor positioned to rotate the test motor in a reverse direction prior to the commencement of the test.
Figure 2:
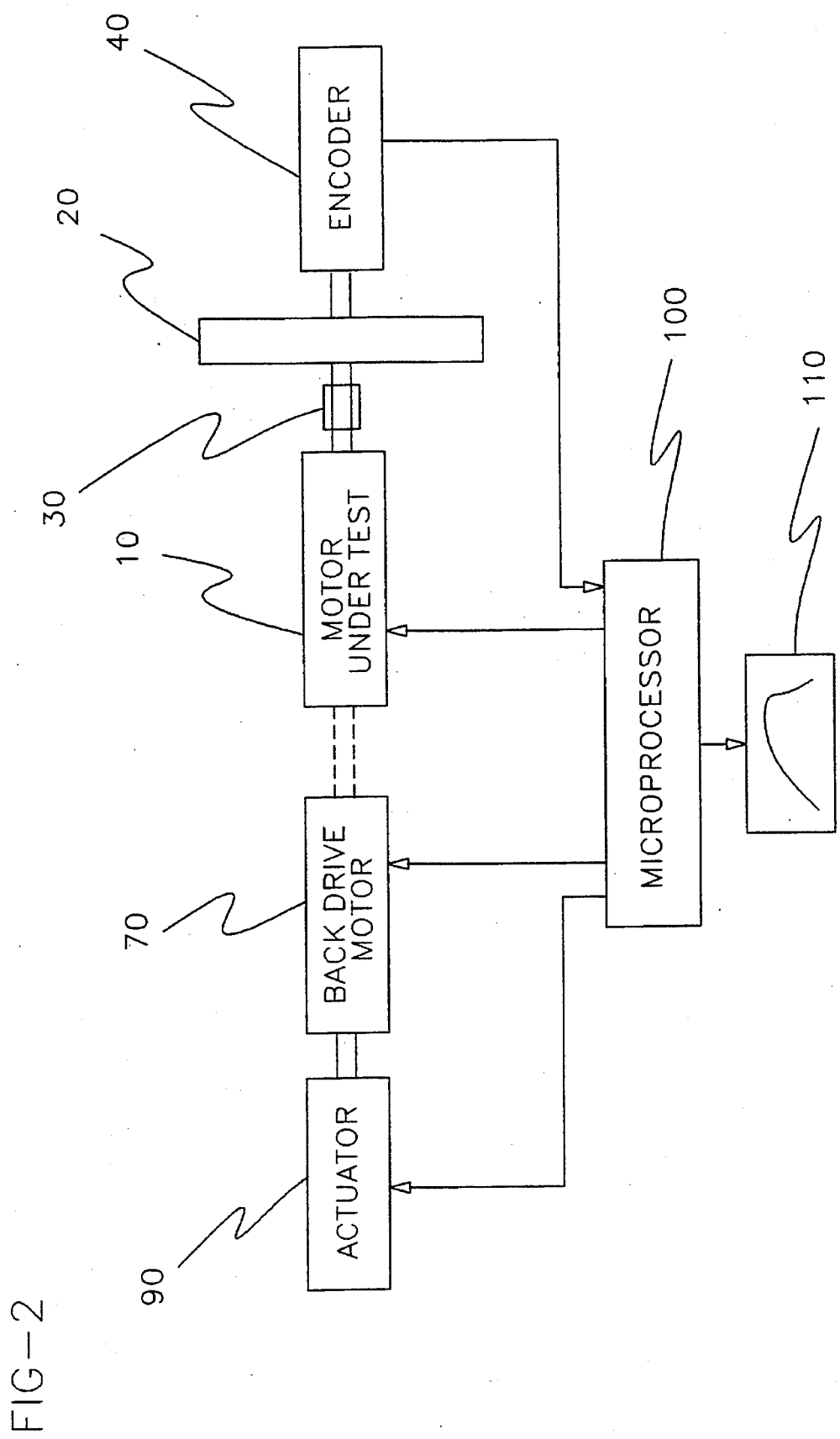
FIG. 2 is a simplified block diagram of the test arrangement shown in FIG. 1.

Referring now to the drawings which illustrate a preferred embodiment of the invention, and particularly to FIGS. 1 and 2, a motor under test 10 is shown having an output shaft 15 connected to a flywheel 20 by means of a coupling 30. The flywheel in turn is connected to an encoder 40. The coupling 30 allows the motor under test to be installed and removed quickly. The digital encoder and flywheel are supported on a test fixture 50 by means of low friction bearings 60.

As shown in FIGS. 1 and 2, a back drive motor 70 is provided with a back drive wheel 80 which may engage the motor shaft coupling 30 or some other part of the rotating system to impart a backward or reverse direction rotation to the motor shaft ]5. The back drive wheel is brought into engagement with the motor shaft coupling 30 by means of an actuator 90. As shown in Fig. 1, the back drive motor 70 is mounted on a lever and the actuator 90 is an air cylinder which can bring the back drive wheel into contact with the coupling 30.

In FIG. 2, a microprocessor 100 controls the operation of the actuator 90, the back drive motor 70 and the motor Lander test 10 and receives data from the encoder 40 which is processed and applied to an output device shown generally at 110 which provides a torque versus speed output for that particular motor.

Figure 3:
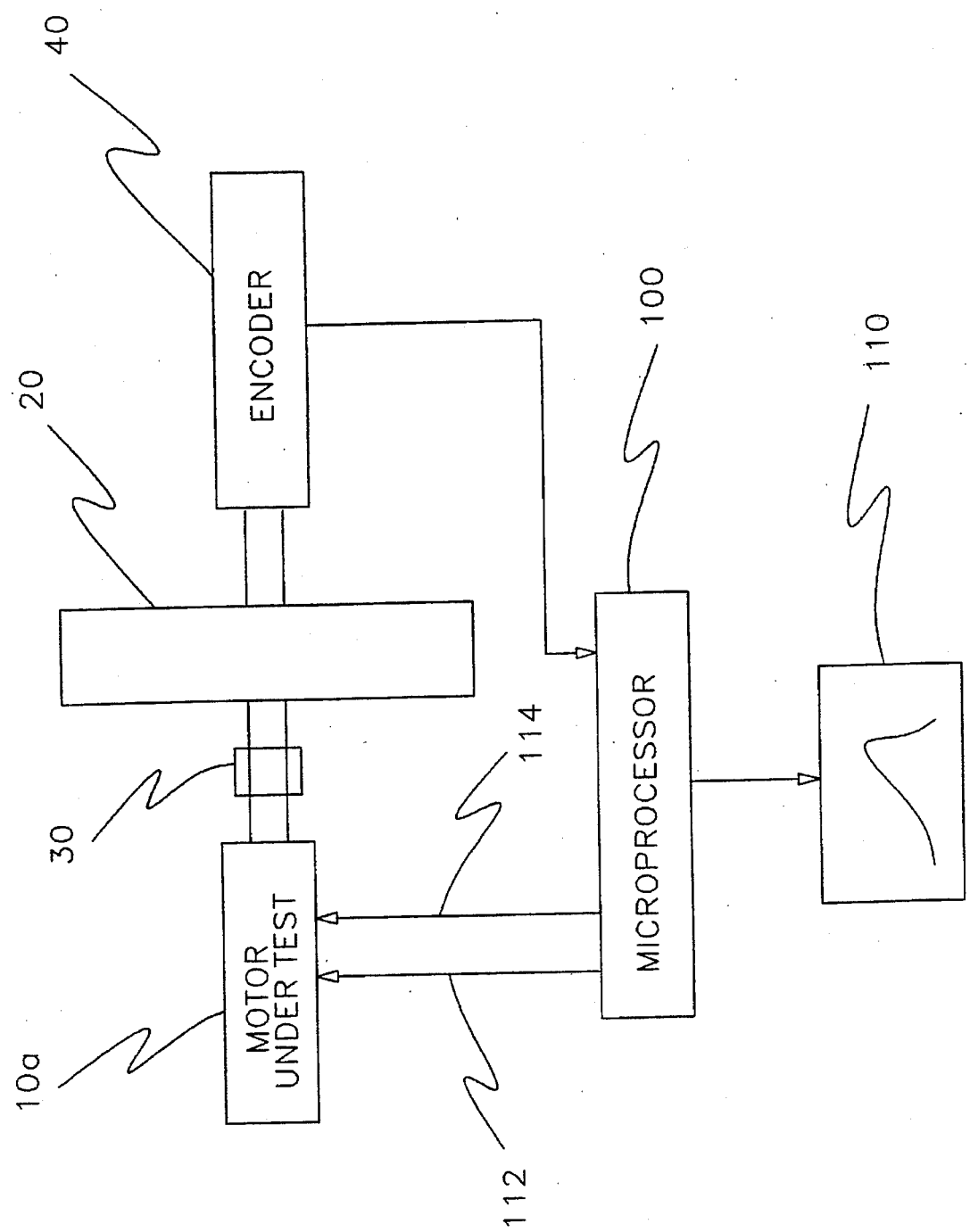
FIG. 3 is a simplified block diagram showing another embodiment of the invention where the motor under test can be rotated in the reverse direction under control of a microprocessor.

Alternatively, the arrangement shown in FIG. 3 may be used with those motors which are capable of being operated in the reverse direction merely by proper application of electric power thereto. In this embodiment, the microprocessor 100 would first apply power to the motor 10A on line 112 to rotate the motor in the reverse direction, and then provide power on line 114 to operate the motor in its normal direction of rotation.

Figure 4:
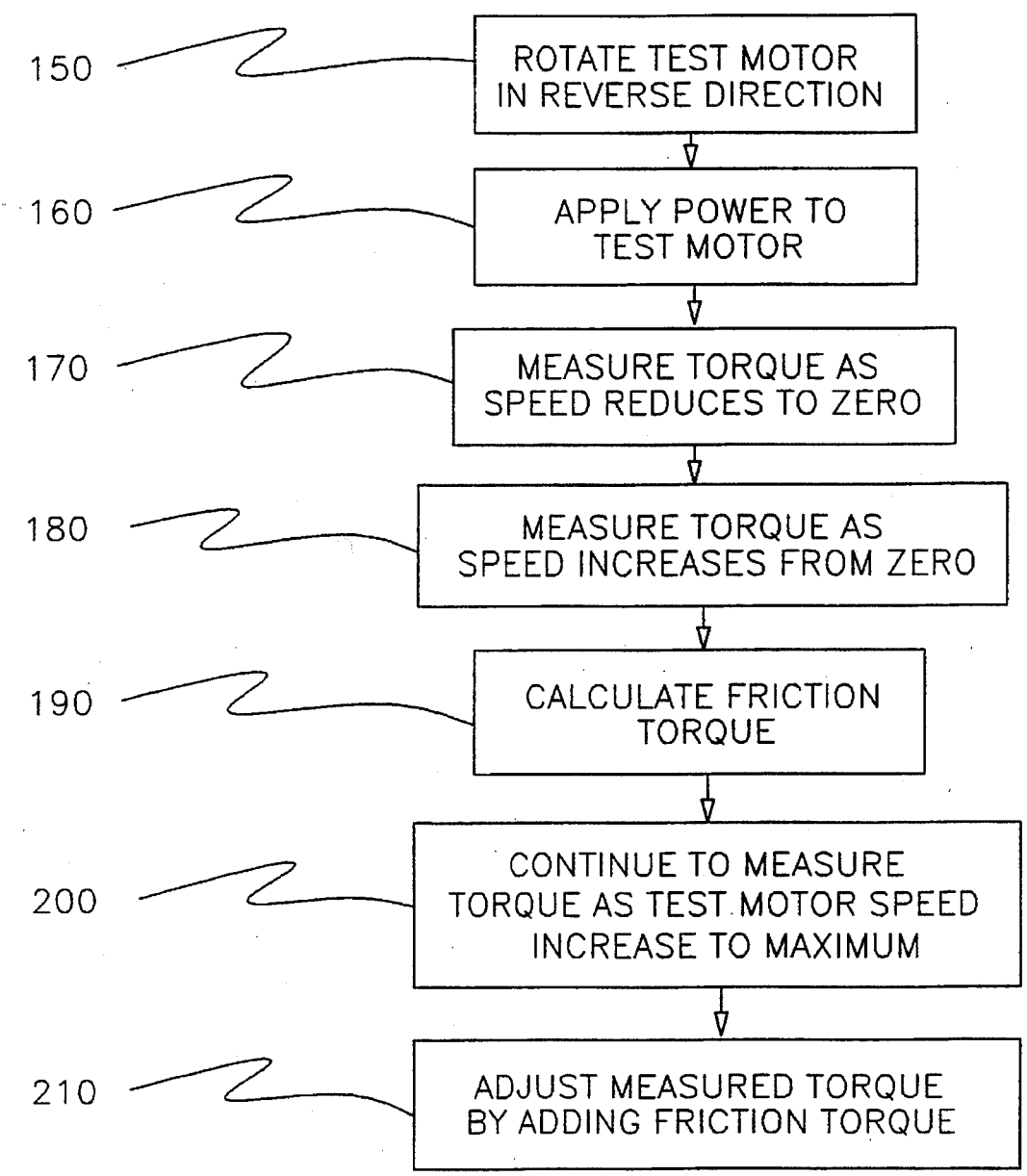
FIG. 4 is a flow chart showing the steps used in the method and apparatus of the present invention.

Referring now the flow chart of FIG. 4, step 150 calls for the test motor to be rotated in the reverse direction. As mentioned above, this may be accomplished in several ways: electronically, by proper application of electrical power to the motor: mechanically, through the use of a back drive motor 70; or mechanically, by manually rotating the motor in the reverse direction. In any case, it is desired that the motor be rotated relatively slowly, in the order of 100 rpm, in the case of an 1800 rpm motor.

Once the motor is rotating freely in the a reverse direction, power is applied to the test motor 10 in step 160. This will cause the output shaft of the motor to tend to rotate in the forward direction. Of course, since the motor is rotating in the opposite direction at this time, it will cause the motor shaft 15 first to stop, and then reverse direction.

As the motor output shaft speed decreases from 100 rpm to zero rpm, the torque of the motor is being measured by digital encoder 40 and microprocessor 100, as described in U.S. Pat. No. 5,218,60. This accomplished in step 170 of FIG. 4. Preferably, the torque is averaged during this interval. This represents the locked rotor torque plus friction torque or (TM+TF). Both the electrical power applied to the motor and the friction torque are combining to slow and eventually stop the motor shaft.

In step 180, torque is measured as the speed of the motor shaft increases from zero rpm to some predetermined low speed in the normal direction. For an 1800 rpm motor, this predetermined low speed may be in the order of 50 rpm. The torque is averaged from near zero rpm to 50 rpm. The measure torque value is the locked rotor torque minus friction torque, or (TM−TF).

Friction torque is calculated in step 190 by subtracting the torque measured in step 170 from the torque measured in step 180. In other words, (TM+TF)− (TM−TF). This yields a value which is twice the friction torque, and merely taking one-half this value will yield friction torque TF.

Figure 5:
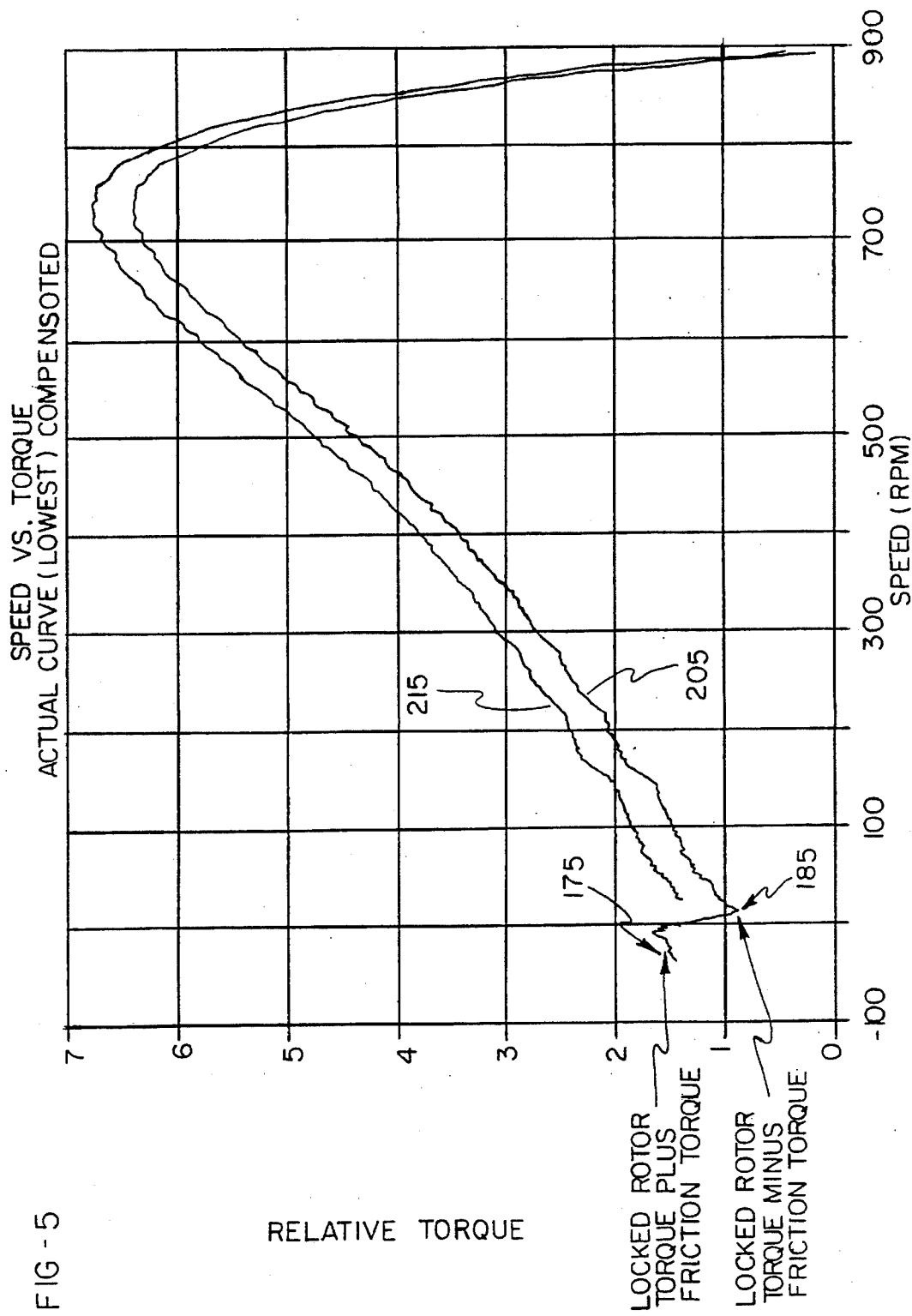
FIG. 5 is a speed versus torque chart showing the output of a typical motor under test.

In step 200, the torque of the motor is measured as the motor speed increases to maximum value. In step 210, the measured torque is then adjusted by adding to it the value of the friction torque. This is illustrated in FIG. 5. The combined locked rotor torque TM and the friction torque TF measured in step 170 is shown in the region 175 of curve 205; the difference between locked rotor torque TM and friction torque TF, as measured in step 180, is shown as the torque value in the region 185. The friction torque TF therefore represents one-half the difference between these two torque values.

The remainder of curve 200 in FIG. 5 represents the measured torque curve, as determined by the method and apparatus described in U.S. Pat. No. 5,218,860. Curve 215, on the other hand, 5 shows an adjustment made to the measured torque (curve 205) which includes the friction torque TF, thus giving the actual torque output of the motor throughout its acceleration to maximum speed.

While the form of apparatus herein described constitutes a preferred embodiment of this invention, it is to be understood that the invention is not limited to this precise form of apparatus and that changes may be made therein without departing from the scope of the invention, which is defined in the appended claims.

What is claimed is:

1. Method for testing electric motors to determine friction torque comprising the steps of mechanically connecting an output shaft of a motor to be tested in a test fixture which includes a torque measuring device, rotating the output shaft of the test motor to rotate the output shaft in a direction reverse to that which the motor normally rotates when electrical power is applied thereto, electrically connecting electrical power to the test motor to cause the output shaft to rotate in its normal direction, measuring the average torque of the motor as the speed of the output shaft decreases to zero, measuring the average torque of the motor as the speed of the output shaft increases from zero to a predetermined low speed in the normal direction, and calculating friction torque by dividing by two the difference between the average torque value calculated as the output shaft speed decreases to zero and the average torque value calculated as the output shaft speed increases from zero to a predetermined low speed, determining the actual torque of a motor at various speeds by adding the friction torque to the measured motor torque.

\* \* \* \* \*